(12) United States Patent
Baumann

(10) Patent No.: US 8,372,129 B2
(45) Date of Patent: *Feb. 12, 2013

(54) WARMING DEVICE

(76) Inventor: Nicholas R. Baumann, White Bear Lake, MN (US)

( * ) Notice: Subject to any disclaimer, the term of this patent is extended or adjusted under 35 U.S.C. 154(b) by 127 days.

This patent is subject to a terminal disclaimer.

(21) Appl. No.: 12/802,163

(22) Filed: Jun. 1, 2010

(65) Prior Publication Data

US 2010/0263678 A1    Oct. 21, 2010

Related U.S. Application Data

(63) Continuation of application No. 11/359,143, filed on Feb. 22, 2006, now Pat. No. 7,763,060.

(51) Int. Cl.
*A61F 7/00* (2006.01)
(52) U.S. Cl. .......... 607/96; 607/104; 607/107; 607/108; 607/112; 128/849; 601/6; 601/11

(58) Field of Classification Search ................. 128/847, 128/849, 853; 607/96, 104, 107–112; 601/6, 601/11–16; 5/284, 421–423; 219/211, 212
See application file for complete search history.

(56) References Cited

U.S. PATENT DOCUMENTS

2004/0225341 A1* 11/2004 Schock et al. ................ 607/104

* cited by examiner

*Primary Examiner* — Patricia Bianco
*Assistant Examiner* — Keri J Nelson

(57) ABSTRACT

A patient warming device includes a gasket coupled to an interior surface of a base film to define a target region that is attachable to a body surface of a patient. The base film extends from a perimeter of the gasket to provide a surgical drape. An evacuation port is in fluid communication with the target region. When attached to the patient, suction applied to the target region via the evacuation port vasodilates the body surface of the patient such that a heat source communicating with the target region increases a core temperature of the patient.

5 Claims, 5 Drawing Sheets

WARMING DEVICE

BENEFIT CLAIM TO PRIOR NON-PROVISIONAL APPLICATION

This application is a continuation of prior application Ser. No. 11/359,143, filed on Feb. 22, 2006 and now issued as U.S. Pat. No. 7,763,060.

FIELD OF THE INVENTION

Embodiments of the present invention relate to surgical drapes, and more particularly, to surgical drapes and a system useful in warming a patient's core body temperature during surgery.

BACKGROUND

Hypothermia in surgical patients has been shown to significantly increase the risk of surgical site infection and is associated with an increase in post-operative recovery time.

More than 40 million in-patient surgical procedures are performed annually in the United States. During each surgical procedure, each member of the surgical team wears a gown to prevent the transmission of infection from the health care worker to the patient, and each patient is draped with a drape that defines a sterile field that minimizes the transfer of microorganisms between non-sterile areas and the surgical wound.

In general, the patient is minimally clothed, and the operating room is maintained at a temperature of about 68° F. The operating room is maintained at a cool temperature to prevent the healthcare workers from overheating, or becoming uncomfortably warm during the procedure. In practice, the Association of Operating Room Nurses (AORN) and the Center for Disease Control and Prevention (CDC) support the American Institute of Architects Academy of Architecture recommendation that operating room temperatures be maintained between 68° F. and 73° F. However, operating room temperatures are often maintained at less than 68° F. due to surgeon preference, especially in cases where orthopedic surgeons, for example, wear added layers of protective clothing.

Nearly every surgical procedure employs some form of anesthesia. Studies have shown that anesthesia impairs the body's thermal regulatory process. In this regard, the core body temperature of a patient (i.e., the internal organ temperature) decreases a couple of degrees Celsius during surgery due simply to being anesthetized. In addition, most patients experience post anesthetic tremors (shivers). These shivers can break down body tissue, increase infection rates, and increase the time it takes for wounds to heal, all of which increase the time it takes the patient to recover from the surgical procedure. Moreover, the presence of anesthesia, in addition to impairing the thermal regulatory function of the patient, also constricts the blood vessels in the patient. This effect is termed vasoconstriction and is the body's attempt to insulate itself against further heat loss. Therefore, there is cyclical pattern of events during a surgical procedure that places the patient at risk of hypothermia: the use of anesthesia drops the patient's core temperature and reduces the patient's thermal regulation ability, and the cold patient experiences a constriction of blood vessels that impairs the body's ability to warm up.

There are negative consequences for patients who experience hypothermia. The negative consequences include adverse myocardial events, impaired platelet function, coagulopathy, reduced medication metabolism, including reduced metabolism of anesthesia, shivering which can lead to damage of body tissue, impaired wound healing, and increased risk of surgical site infection.

One conventional approach to warming a patient post surgically includes wrapping the patient's body in warm cotton towels. For the above reasons, an anesthetized patient is physiologically impaired from efficiently warming up after surgery. Post surgically, the patient will typically regain heat (i.e., warm up) at a rate of about one degree Celsius per hour. Thus, an extended period of time is required to warm the patient, which puts the patient at risk to surgical site infection and, at a minimum, increases post operative recovery time.

Certain conventional patient drapes provide a warm air flow over a patient during surgery. These conventional "warming drapes" blow heated air over the patient during surgery, and optionally, postoperatively. However, for the reasons described above, the anesthetized patient experiences a constriction of blood vessels that limits the effectiveness of convectively warming the patient. In addition, the forced flow of warm air has been associated with the undesired movement of debris onto the sterile field.

For these and other reasons, there is a need for the present invention.

SUMMARY

One aspect of the present invention relates to a flexible drape useful for warming a patient during surgery. The drape includes a base film defining a target region, means for attaching the base film to a body surface of the patient, and an evacuation port in fluid communication with the target region. In this regard, the evacuation port is configured to negatively pressurize the target region and vasodilate the body surface of the patient adjacent the target region.

Another aspect of the present invention relates to a drape system for warming a patient during a surgical procedure. The drape system includes a drape, a heat source, and a suction device. The drape includes a base film defining a target region, means for attaching the base film to a body surface of the patient, and an evacuation port in fluid communication with the target region. The heat source communicates with the base film. The suction device is coupled to the evacuation port and is configured to form a negative local pressure between the target region and the body surface of the patient. In this regard, the negative local pressure vasodilates the body surface, and the vasodilated body surface increases heat transport away from the heat source and into a core of the patient.

Another aspect of the present invention relates to a method of increasing a core temperature in a patient during surgery. The method provides draping a body surface of the patient with a drape including a target region and an evacuation port in fluid communication with the target region. The method additionally provides evacuatively vasodilating the body surface adjacent to the target region. The method further provides transporting heat across the body surface and into a core of the patient.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
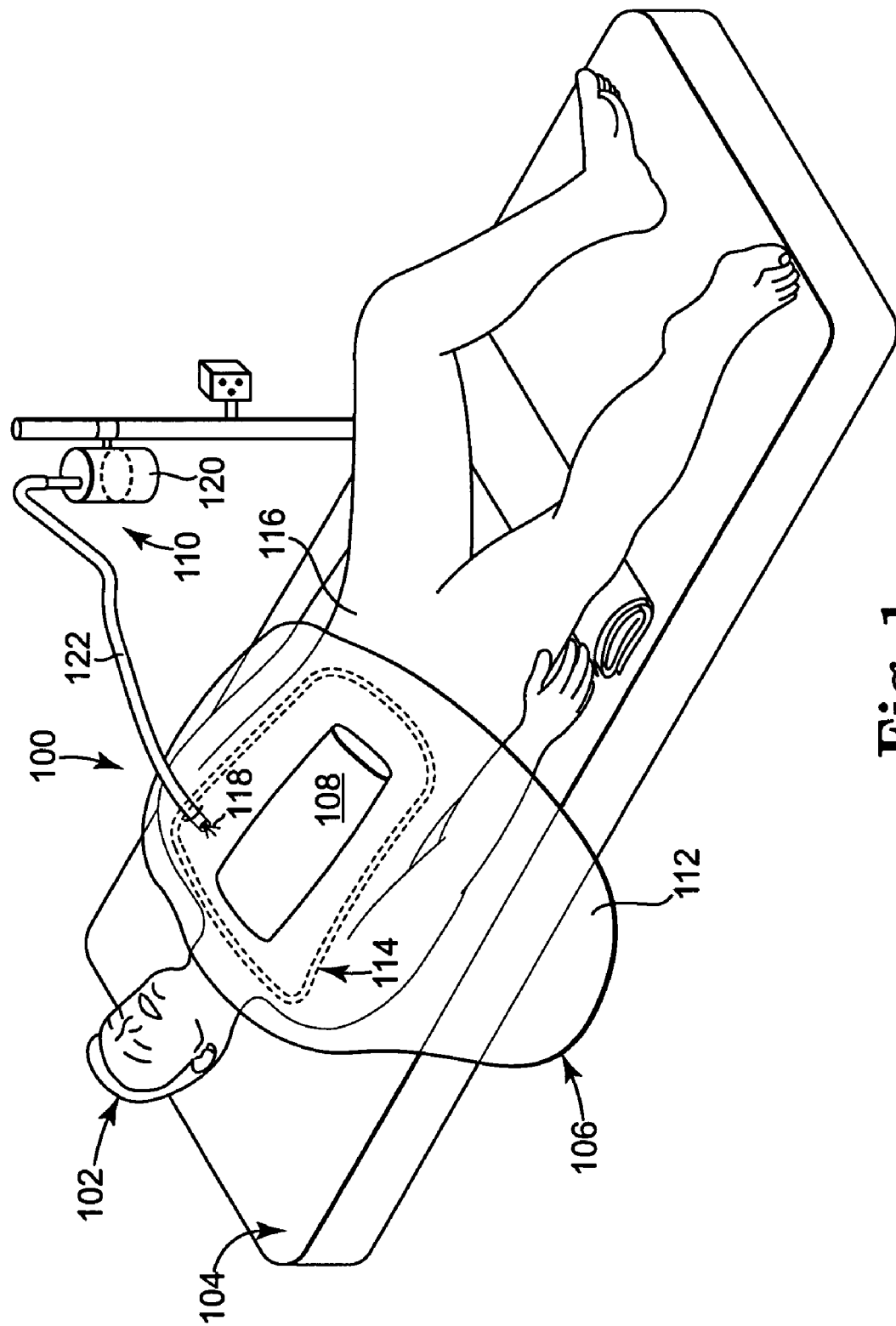
FIG. 1 illustrates a perspective view of a drape system useful for warming a patient during a surgical procedure according to one embodiment of the present invention.

FIG. 1 illustrates a perspective view of a drape system 100 useful for warming a patient 102 during a surgical procedure according to one embodiment of the present invention.

In one embodiment, the patient 102 reclines on an operating room (OR) table 104, and the drape system 100 includes a drape 106, a heat source 108 communicating with the drape 106, and a suction device 110 coupled to the drape 106. The drape 106 is flexible and includes a base film 112 defining a target region 114, means for attaching the base film 112 to a body surface 116 of the patient 102, and an evacuation port 118 communicating with the target region 114. In one embodiment, the suction device 110 includes a vacuum pump 120, and tubing 122 fluidly connected between the evacuation port 118 and the pump 120.

The drape system 100 is useful for warming the patient 102 during a surgical procedure. In particular, the suction device 110 is configured to form a negative local pressure between the target region 114 and the body surface 116 of the patient 102; the negative local pressure vasodilates the body surface 116, such that the vasodilated body surface increases heat transport away from the heat source 108 and into core organs of the patient 102.

In one embodiment, the drape 106 is a sterile drape suited for use in a sterile field procedure, although it is to be understood that the drape 106 could be employed outside the sterile field. In another embodiment, the drape 106 is a non-sterile drape suited for use in a non-sterile field, for example on a back of the patient 102, outside of the sterile field during a chest procedure.

Aspects of the invention provide the drape 106 beneficially coupled to the body surface 116 of the patient 102, such as on a chest of the patient 102 as illustrated in FIG. 1. It is to be understood that the drape 106 can be disposed on any body surface of the patient 102. For example, aspects of the invention provide the drape 106 adhered to a body surface of the patient 102 over organs associated with high volumetric blood flow. In one embodiment, the drape 106 is adhered to a body surface of the patient 102 over the kidney region. In other embodiments, the drape 106 is adhered to a body surface of the patient 102 over the heart, axillary to an arm, over the femoral artery in a leg, or over a portion of the head. While not bound to this theory, vasodilating a body surface of the patient 102 creates a pathway for circulating blood to carry heat from the patient's body surface to a core of the body (i.e., through the heart), and when coupled with the heat source 108, the "warmed" blood flow transports the added heat directly into an internal core of the patient 102.

Figure 6:
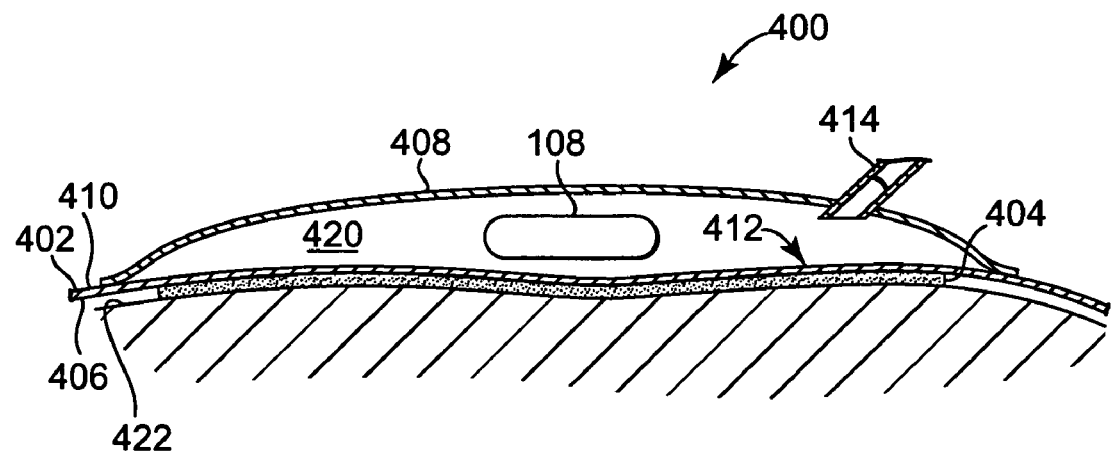
FIG. 6 illustrates a cross-sectional view of a drape according to another embodiment of the present invention.

Suitable materials for the base film 112 of the drape 106 include polymeric films, in general. In one embodiment, the drape 106 is formed of polyethylene and gamma sterilized. In other embodiments, the drape 106 is formed from a polymeric film suited for steam and/or ethylene oxide and/or gamma radiation sterilization. Exemplary materials for the base film 112 include polyethylene, polypropylene, block co-polymers such as polybutylene, polyester, or blends and/or co-polymers of these polymeric materials. In one embodiment that is best illustrated in FIG. 6, the base film is a thin incise drape, such as a Steri-Drape™ incise drape or an Ioban™ incise drape, available from 3M Company, St. Paul, Minn.

In one embodiment, the heat source 108 includes a dry chemical heat source contained within a packet. Suitable dry chemical heat sources include Grabber MYCOAL™ heat packets, available from L+M Distributors, Inc., Smyrna, Del. Other suitable heat sources include therapeutic heat pads such as a TheraTherm™ Digital Moist Heating Pad, available from PainReliever.com of Wichita, Kans.

In one embodiment, the heat source 108 includes an air activated warming pad available from, for example, Heat Factory, Vista, Calif. In another embodiment, the heat source 108 includes a reusable liquid pad such as a Thermo-pad, available from Hood Thermo-Pad, Summerland, BC, Canada.

In one embodiment, the heat source 108 includes a fluid system configured to circulate warm fluid (i.e., a fluid having a temperature of greater than 90 degrees Fahrenheit, preferably a temperature of greater than 98 degrees Fahrenheit) across the target region 114. Suitable fluids circulating systems include hot water bottles, or pressurized re-circulating fluid systems employed in operating rooms generally. One suitable fluid circulating system includes an Artic Sun® temperature-controlled water packet, identified as a model 100 and available from Kimberly-Clark Health Care, Roswell Ga. In any regard, the heat source 108 communicates with the base film 112 to provide heat that is efficiently and directly carried from the vasodilated body surface to core internal portions of the body of the patient. In one embodiment, the heat source 108 is disposed on an upper surface of the base film 112, as illustrated in FIG. 1. In another embodiment, the heat source 108 is disposed in the target region between the base film and the body surface of the patient, as best illustrated in FIG. 6.

In one embodiment, suction device 110 is configured to form a negative local pressure between the target region 114 and the body surface 116 of the patient to vasodilate vessels adjacent to the body surface 116. In general, the suction device 110 is suited for pulling a vacuum of between zero and 500 millimeters of mercury (i.e., −500 mm Hg), although local evacuated pressures in the target region 114 of about 50 mm Hg should initiate a vasodilation of the body surface, thus opening a pathway for heat into a core of the body. A suitable suction unit includes a Gomco® Portable Suction Unit, available from Armstrong Medical Industries, Inc., Lincolnshire, Ill. Other suitable suction units/devices providing a greater vacuum level are also acceptable.

Figure 2:
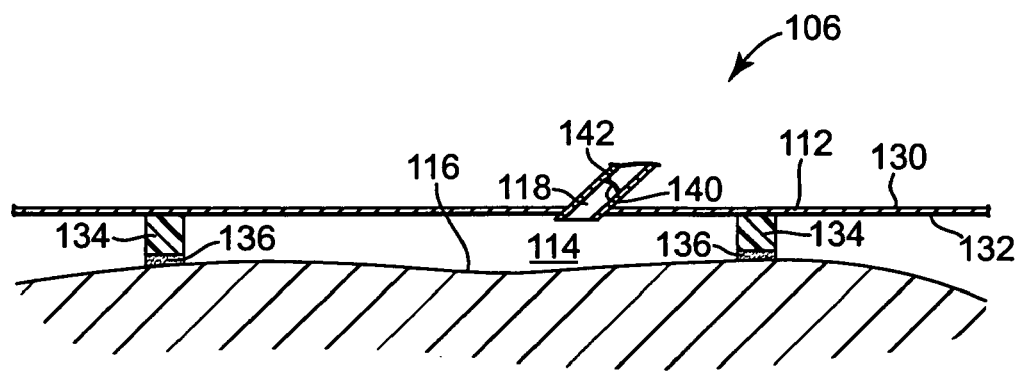
FIG. 2 illustrates a cross-sectional view of a drape according to one embodiment of the present invention.

FIG. 2 illustrates a cross-sectional view of the drape 106 according to one embodiment of the present invention. In one embodiment, the base film 112 defines an exterior surface 130 opposite an interior surface 132. In one embodiment, the means for attaching the base film 112 to the body surface 116 includes a gasket 134 coupled to the interior surface 132 of the base film 112 and a layer of adhesive 136 disposed on a surface of the gasket 134.

Suitable materials for the gasket 134 include rubber, for example styrene butadiene-based rubber, foam, gels and the like. In one embodiment, the gasket 134 is an annular foam core 134, such as a closed cell foam core adhered to the interior surface 132 of the base film 112. In this manner, the foam core 134 combines with the base film 112 to define the target region 114 that has a boundary defined by opposing portions of the foam core 134.

In one embodiment, the adhesive 136 is coated onto the gasket 134 and includes a release liner (not shown) suited for removal such that the adhesive 136 can be adhered to the body surface 116. When in an operative condition, the adhesive 136 secures the drape 106 to the body surface 116, and the evacuation port 118 is in fluid communication with the target region 114, such that the suction device 110 (FIG. 1) can be operated to evacuate the target region 114 and effectively suction the base film 112 to the body surface 116, and negatively pressurize the target region 114 adjacent to the body surface 116.

A negative local pressure adjacent the body surface 116 is developed that causes vessels adjacent to the body surface 116 to vasodilate. The vasodilated body surface is characterized by an increase in blood flow across the body surface such that the heat source 108 (FIG. 1) efficiently and rapidly transfers heat from the heat source 108 into a core, for example core organ, of the patient 102. In this regard, the heat source 108 can be disposed adjacent the exterior surface 130 of the base film 112. In an alternate embodiment, the heat source 108 is disposed between the interior surface 132 of the base film 112 and the body surface 116 within the target region 114.

In one embodiment, the suction device 110 (FIG. 1) is operated to continuously maintain a negative local pressure in the target region 114 adjacent to the body surface 116. For example, in one embodiment the suction device 110 is continuously operated to maintain a negative pressure in the target region from between 10 mm Hg to 500 mm Hg, preferably from 50-250 mm Hg. In another embodiment, the evacuation port 118 includes a one-way valve 140 disposed within a stem 142 of the evacuation port 118 that permits evacuate to flow from the target region 114 to an exterior of the drape 106, but does not permit air to flow from the room through stem 142 into the target region 114.

Figure 3:
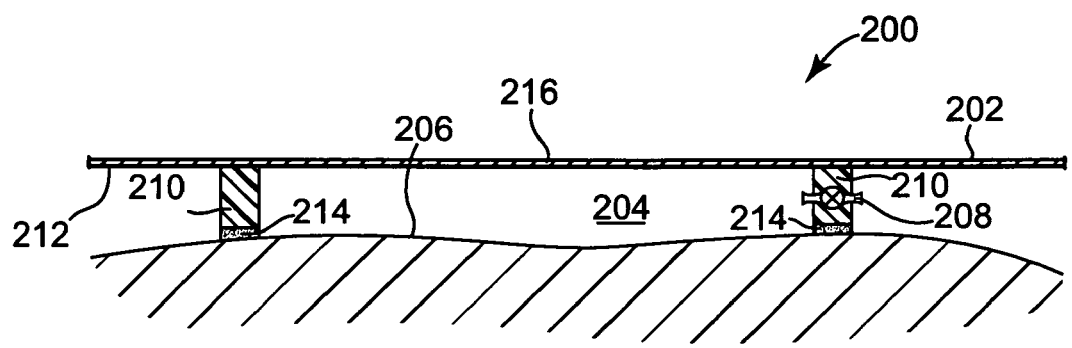
FIG. 3 illustrates a cross-sectional view of a drape according to another embodiment of the present invention.

FIG. 3 illustrates a cross-sectional view of a drape 200 according to another embodiment of the present invention. The drape 200 includes a base film 202 defining a target region 204, means for attaching the base film 202 to a body surface 206 of a patient, and an evacuation port 208 in fluid communication with the target region 204.

In one embodiment, the means for attaching the base film 202 to the body surface 206 includes a gasket 210 coupled to an interior surface 212 of the base film 202 and a layer of adhesive 214 disposed on a surface of the gasket 210. Suitable materials for the gasket 210 include rubber, for example styrene butadiene-based rubber, foam, gels and the like. In one embodiment, the gasket 210 is similar to the gasket 134 (FIG. 2) and is a foam core. In one embodiment, the evacuation port 208 is integrally formed in and through the gasket 210 and is in fluid communication with the target region 208. In one embodiment, the evacuation port 208 defines a one-way valve configured to permit fluid flow to be evacuated from the target region 204.

The evacuation port 208 is coupled to the suction device 110 (FIG. 1), where the suction device 110 evacuates the target region 204 and negatively pressurizes the target region 204 and vasodilates vessels adjacent to the body surface 206 of the patient near the target region 204. In one embodiment, the heat source 108 (FIG. 1) is placed across an exterior surface 216 of the base film 202, and heat is conducted through the base film 202, which is in contact with the body surface 206, and into the patient. In another embodiment, the heat source 108 is disposed in the target region 204 between the base film 202 and the body surface 206 prior to a suction device 110 evacuating the target region 204 via the evacuation port 208. As a point of reference, during evacuation by the suction device 110, the base film 202 is collapsed onto the body surface 206.

Figure 4:
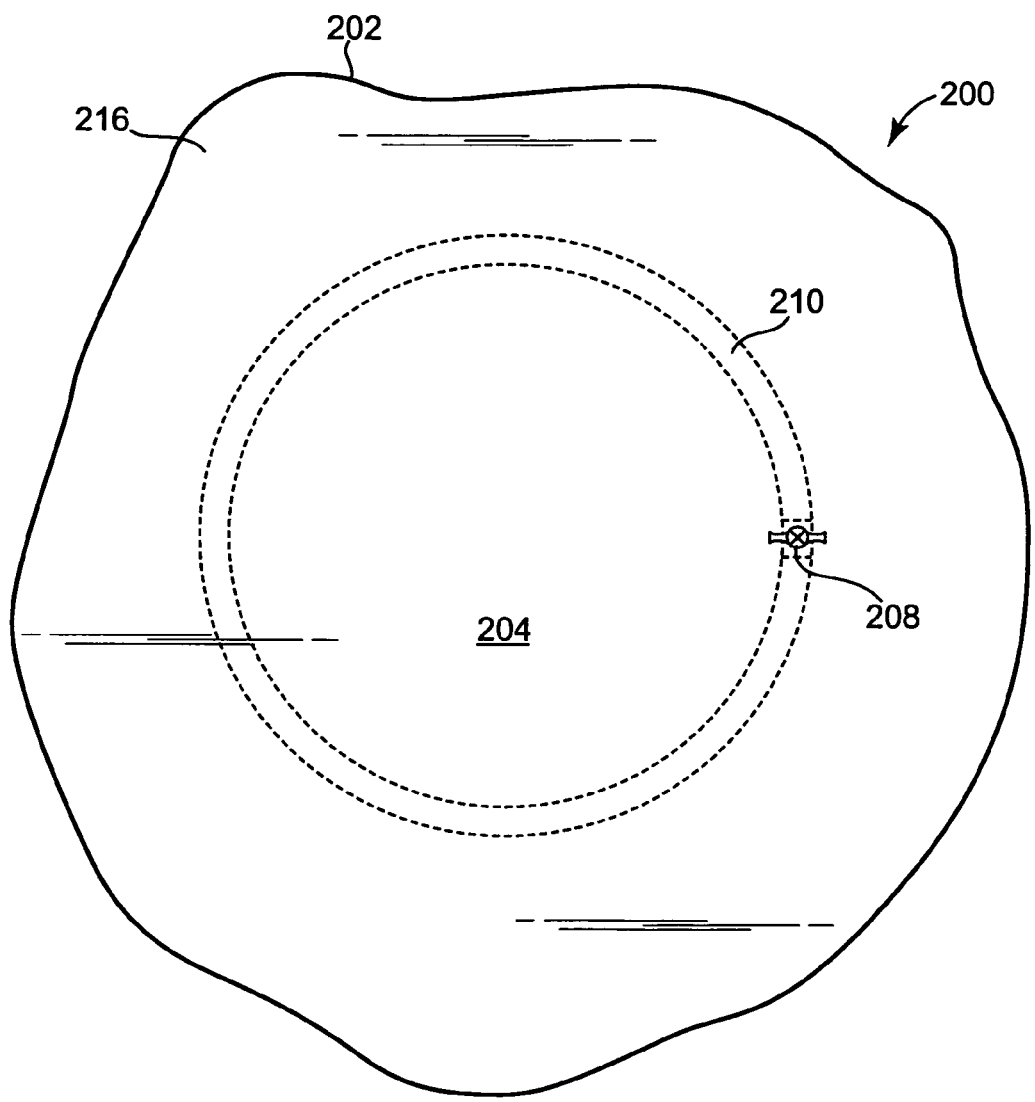
FIG. 4 illustrates a top view of the drape illustrated in FIG. 3 according to one embodiment of the present invention.

FIG. 4 illustrates a top view of the drape 200. The exterior surface 216 of the base film 202 is oriented up in the view of FIG. 4, and the evacuation port 208 extends through the annular gasket 210 to communicate with the target region 204. During an evacuation procedure of the target region 204, tubing 122 (FIG. 1) is connected to the evacuation port 208 and extends to a suction pump, for example the pump 120 (FIG. 1). In this regard, the tubing 122 is underneath the base film 202 such that the exterior surface 216 of the drape 200 is not cluttered with tubing.

Figure 5:
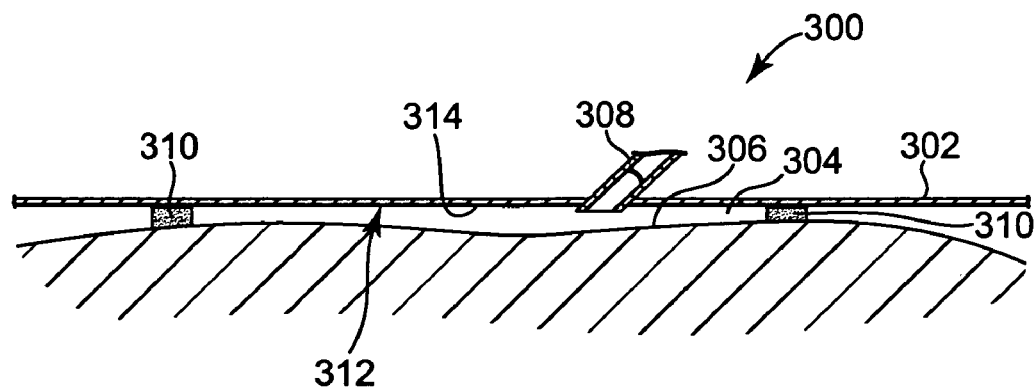
FIG. 5 illustrates a cross-sectional view of a drape according to another embodiment of the present invention.

FIG. 5 illustrates a cross-sectional view of a drape 300 according to another embodiment of the present invention. The drape 300 includes a base film 302 defining a target region 304, means for attaching the base film 302 to a body surface 306 of a patient, and an evacuation port 308 in fluid communication with the target region 304. In one embodiment, the means for attaching the base film 302 to the body surface 306 of the patient includes a bead 310 of adhesive encircling a non-adhesive area 312 of an interior surface 314 of the base film 302. In one embodiment, the evacuation port 308 is coupled to the base film 302 and is in fluid communication with the target region 304 via the non-adhesive area 312.

In one embodiment, the bead 310 of adhesive is a high water content adhesive. Suitable high water content adhesives include adhesives employed to attach conductive medical electrodes to a body, such as EKG and other electrodes. Suitable high water content adhesives include PermaGel™ hydrogel adhesives, available from Tyco Healthcare, Uni-Patch, Wabasha, Minn.

As illustrated in FIGS. 3-5, the target region 204 and 304 are sealed to and displaced away from the body surface 206, 306, respectively. That is to say, in one embodiment the base film in an area of the target region is displaced away from the body surface. In this manner, evacuation of the target region will negatively pressurize the target region and vasodilate vessels of the body surface of the patient adjacent to the target region.

FIG. 6 illustrates a cross-sectional view of a drape 400 according to another embodiment of the present invention. The drape 400 includes a base film 402, a layer 404 of adhesive coated onto an interior surface 406 of the base film 402, and a second film 408 coupled to an exterior surface 410 of the base film 402. In one embodiment, the layer 404 of adhesive is continuously coated over an area of the base film 402 to define a target region 412. In one embodiment, an evacuation port 414 is coupled to the second film 408 and is in fluid communication with the target region 412.

The second film 408 is coupled to the exterior surface 410 of the base film 402 about a perimeter of the target region 412 to define a target pocket 420. Exemplary materials for the second film 408 include polyethylene, polypropylene, block co-polymers such as polybutylene, polyester, or blends and/or co-polymers of these polymeric materials. As a point of reference, the heat source 108 is disposed within the target pocket 420.

During use, the layer 404 of continuous adhesive attaches the base film 402 to a body surface 422 of a patient, and the evacuation port 414 in combination with the suction device 110 (FIG. 1) evacuates the target pocket 420 to negatively pressurize the target region 412 and vasodilate vasculature of the body surface 422 of the patient adjacent to the target region 412. In this regard, the base film 402 and the adhesive 404 are preferably thin, pliant materials suited to conform over a body surface and respond to the pressurization or suction of the suction device 110. In one embodiment, a suitable combination of base film 402 and adhesive 404 includes, for example, an incise drape as identified above and including a thin barrier film and a continuous layer of adhesive coated on one side of the thin film.

In one embodiment, the adhesive 404 is a high water content adhesive that conducts heat from the heat source 108 to the vasodilated body surface 422 of the patient. Suitable high water content adhesives include adhesives employed to attach conductive medical electrodes to a body, such as EKG electrodes and other electrodes. Suitable high water content adhesives include PermaGel™ hydrogel adhesives, available from Tyco Healthcare, Uni-Patch, Wabasha, Minn.

Figure 7:
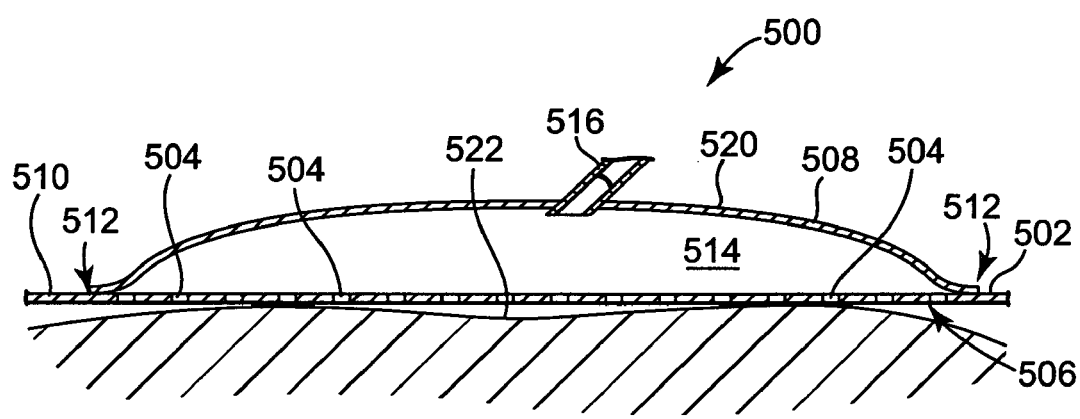
FIG. 7 illustrates a cross-sectional view of a drape including a porous base film according to one embodiment of the present invention.

FIG. 7 illustrates a cross-sectional view of a drape 500 according to another embodiment of the present invention. The drape 500 includes a base film 502 that defines a plurality of pores 504 distributed across a target region 506, and a second film 508 coupled to an exterior surface 510 of the base film 502 about a perimeter 512 of the target region 506 to define a target pocket 514 between the second film 508 and the base film 502. In one embodiment, the base film 502 is a polyethylene film defining a macro-porous array of pores 504. Films suitable for porous base film 502 are available from Tredegar Films Products, Richmond, Va.

In one embodiment, an evacuation port 516 is coupled to the second film 508, where the evacuation port 516 is in fluid communication with the target region 506 via the target pocket 514. In one embodiment, a heat source, for example, heat source 108 of FIG. 1, is disposed on an exterior side 520 of the second film 508 and transfers heat through the drape 500 and through the base film 502. In another embodiment, the heat source 108 is disposed within target pocket 514.

During use, a suction device, for example suction device 110 of FIG. 1, is coupled to the evacuation port 516 to evacuate the target pocket 514. In evacuating the target pocket 514, the suction device 110 suctions the porous base film 502 onto a body surface 522 of a patient.

Various embodiments of the present invention have been described that permit heating and increasing a core body temperature of an anesthetized patient during a surgical procedure. For example, a drape system has been described that includes a flexible drape, a heat source, and a suction device. The flexible drape includes a base film defining a target region, means for attaching the base film to a body surface of the patient, and an evacuation port in fluid communication with the target region. The heat source communicates with the base film. The suction device is coupled to the evacuation port and when activated, forms a negative local pressure between the target region and the body surface of the patient. The negative local pressure vasodilates vessels adjacent to the body surface to increase heat transport away from the heat source and into a core of the patient.

By the mechanism described above, the vaso-constricted and anesthetized patient whose natural thermoregulatory response is depressed can be intro-operatively warmed by the increased delivery of heat into the blood flowing through the vasodilated vasculature. Patients who are kept warm during surgery generally have quicker recovery times, and are at a reduced risk of acquiring a surgical site infection.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A warming device comprising:
   a base film;
   a second film coupled to the base film to provide a target pocket, the base film defining a plurality of pores distributed across the target pocket, the target pocket sized for placement onto and not around a body surface of a person;
   an evacuation port connected to the second film and in fluid communication with the target pocket;
   wherein suction applied to the evacuation port suctions the target pocket into attachment with the body surface of the person and vasodilates the body surface of the person such that a heat source communicating with the base film transports heat into a core of the person.

2. The warming device of claim 1, wherein the second film is coupled to the exterior surface of the base film on a perimeter of the target pocket.

3. The warming device of claim 1, wherein the heat source is disposed in the target pocket.

4. The warming device of claim 1, wherein the heat source is a heat pack that is configured for placement into the target pocket.

5. A warming device comprising:
   a base film and a pocket having an area attached to the base film;
   an evacuation port in fluid communication with the pocket;
   means for heating the pocket; and
   means for applying suction to the pocket through the evacuation port and thereby attaching the area of the pocket to a body and vasodilating skin of the body and transporting heat from the pocket into a core of the body;
   wherein the area of the pocket attached to the base film is sized for placement on but not around the body.

* * * * *